United States Patent [19]

Nakane

[11] Patent Number: 4,533,673
[45] Date of Patent: Aug. 6, 1985

[54] 7-OXABICYCLOHEPTANE SUBSTITUTED ENAMINONE PROSTAGLANDIN ANALOGS AND THEIR USE IN TREATMENT OF THROMBOLYTIC DISEASE

[75] Inventor: Masami Nakane, Hopewell, N.J.

[73] Assignee: E. R. Squibb & Sons, Inc., Princeton, N.J.

[21] Appl. No.: 573,909

[22] Filed: Jan. 26, 1984

[51] Int. Cl.³ ............... C07D 307/935; A61K 31/557
[52] U.S. Cl. .................................. 514/469; 549/463
[58] Field of Search ..................... 549/463; 424/285

[56]     References Cited
    U.S. PATENT DOCUMENTS

| 4,143,054 | 3/1979 | Sprague | 549/463 |
| 4,187,236 | 2/1980 | Sprague | 549/463 |
| 4,220,594 | 9/1980 | Sprague | 549/463 |
| 4,254,044 | 3/1981 | Sprague | 549/463 |

FOREIGN PATENT DOCUMENTS 0043292  8/1982  European Pat. Off. .
2039909  8/1980  United Kingdom .

Primary Examiner—Henry R. Jiles
Assistant Examiner—Bernard L. Dentz
Attorney, Agent, or Firm—Lawrence S. Levinson; Burton Rodney

[57] ABSTRACT

7-Oxabicycloheptane substituted enaminone prostaglandin analogs are provided having the structural formula

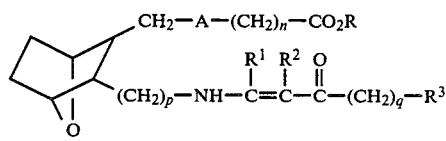

and including all stereoisomers thereof.

The compounds are cardiovascular agents useful, for example, in the treatment of thrombolytic disease.

15 Claims, No Drawings

7-OXABICYCLOHEPTANE SUBSTITUTED ENAMINONE PROSTAGLANDIN ANALOGS AND THEIR USE IN TREATMENT OF THROMBOLYTIC DISEASE

DESCRIPTION OF THE INVENTION

The present invention relates to 7-oxabicycloheptane substituted enaminone prostaglandin analogs which are cardiovascular agents useful, for example, in the treatment of thrombolytic disease. These compounds have the structural formula

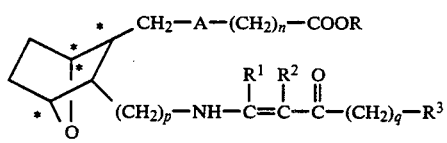

and including all stereoisomers thereof, wherein

A is $CH=CH$ or $(CH_2)_2$, n is 1 to 8, R is H, lower alkyl or alkali metal, p is 1 to 5, q is 0 to 5, $R^1$ and $R^2$ may be the same or different and are hydrogen, lower alkyl or aralkyl, and $R^3$ is lower alkyl, aryl, aralkyl or cycloalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 of any of lower alkyl, halogen (Cl, Br or F), and/or lower alkoxy.

The term "aralkyl", "aryl-alkyl" or "aryl-lower alkyl" as used herein refers to lower alkyl groups as discussed above having an aryl substituent, such as benzyl.

The term "halogen" or "halo" as used herein refers to chlorine, bromine, fluorine or iodine with chlorine being preferred.

The terms "$(CH_2)_n$", "$(CH_2)_p$" and "$(CH_2)_q$" include a straight or branched chain radical having from 1 to 8 carbons in the normal chain in the case of "$(CH_2)_n$", 1 to 5 carbons in the normal chain in the case of "$(CH_2)_p$", and 0 to 5 carbons in the normal chain in the case of "$(CH_2)_q$" and may contain one or more lower alkyl substituents. Examples of $(CH_2)_n$, $(CH_2)_p$ and $(CH_2)_q$ groups include $CH_2$, $CH_2CH_2$, $(CH_2)_3$, $(CH_2)_4$, $(CH_2)_5$, $(CH_2)_6$, $(CH_2)_7$, $$-(CH_2)_2-CH-,\quad -CH_2-CH-,\quad -CH_2-CH-CH-CH_2-,$$
$$\quad\quad\;\;|\quad\quad\quad\quad\;\;|\quad\quad\quad\quad\;\;|\quad\;\;|$$
$$\quad\;\;CH_3\quad\quad\quad\;\;CH_3\quad\quad\;\;CH_3\;CH_3$$

$$-CH_2-CH-CH_2-CH-,$$
$$\quad\quad\;\;|\quad\quad\quad\quad\;\;|$$
$$\quad\;\;CH_3\quad\quad\quad\;\;CH_3$$

(with a $CH_3$ branch on the first example) and the like.

Preferred are those compounds of formula I wherein A is $(CH_2)_2$ or $CH=CH$, n is 2 to 4, R is H, p is 1, q is 0, $R^1$ and $R^2$ are hydrogen and $R^3$ is lower alkyl, aryl such as phenyl, or benzyl.

The various compounds of the invention may be prepared as outlined below.

A. Where p is 1, $R^1$ and $R^2$ are each H

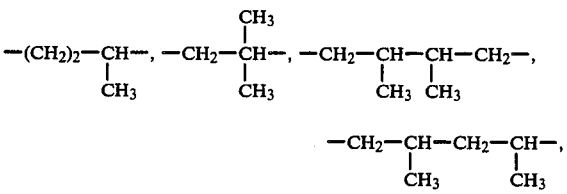

(where A is —CH=CH—)
II                   IIA

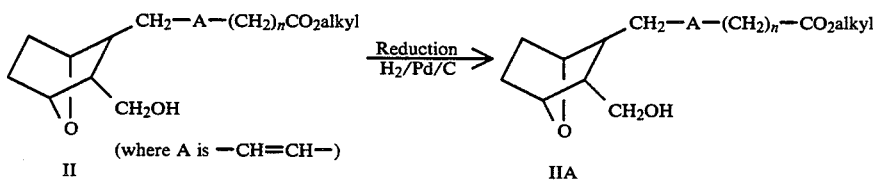

IV

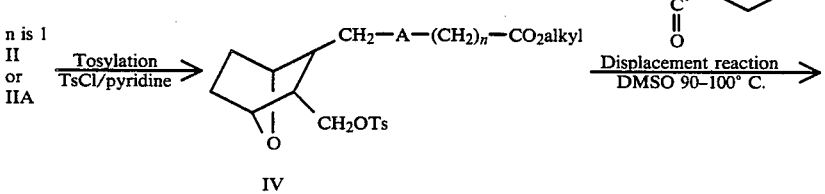

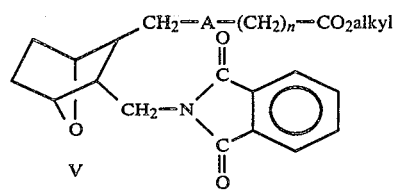
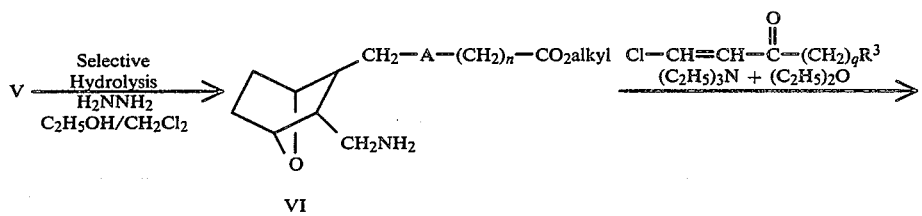
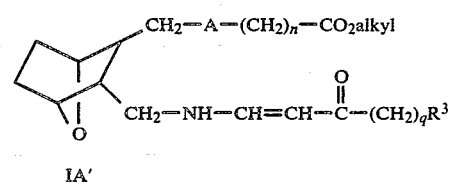
B. Where p is 2 to 5
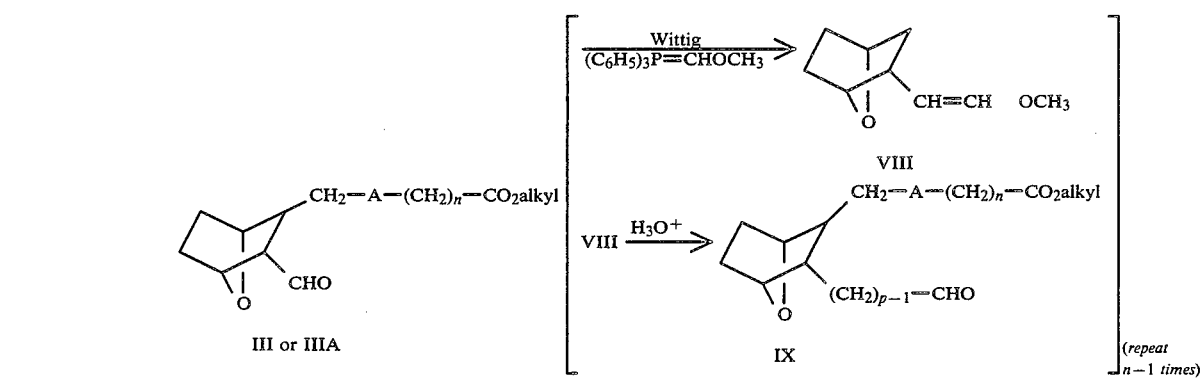
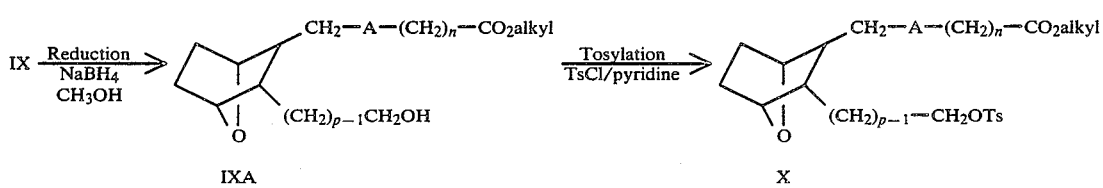
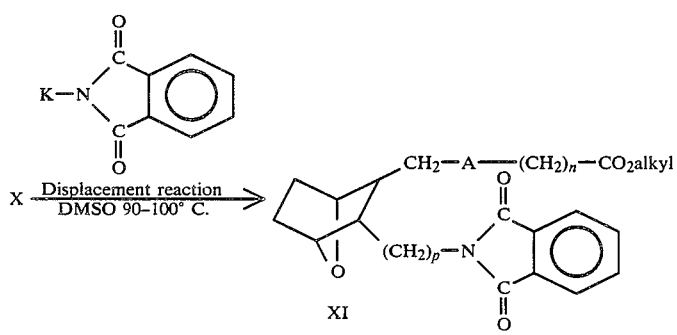

-continued

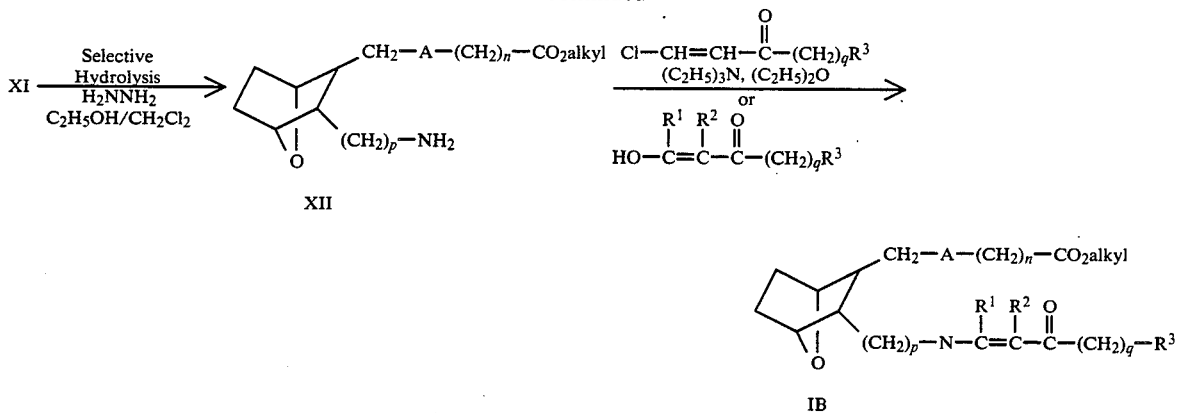

XII

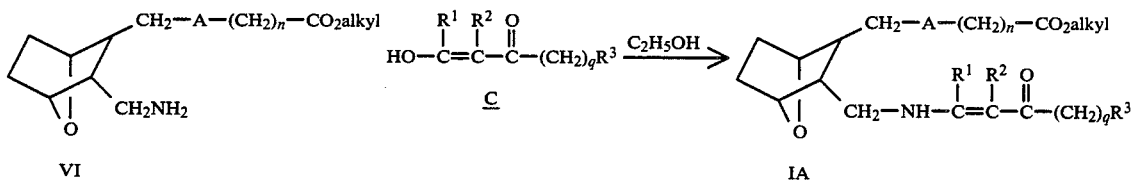

IB

A. Alternative syntheses - where m is 1, p is 1 and $R^1$ and/or $R^2 \neq H$

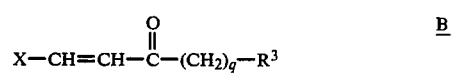

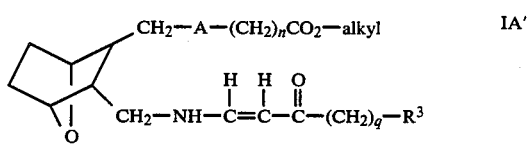

VI    C    IA

As seen in reaction sequence "A", compounds of the invention where p is 1, that is

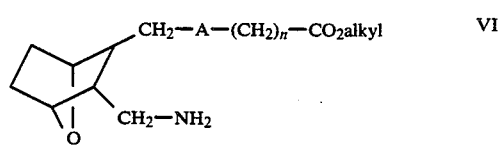  IA are prepared by tosylating the lower alkyl ester containing the hydroxymethyl group, that is, compound II or IIA (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

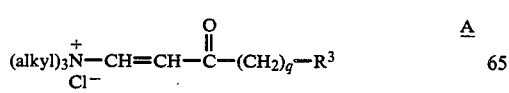  VI

To prepare compounds of formula I where $R^1$ and $R^2$ are each H, the amine VI is then reacted with amine salt A $$\underset{Cl^-}{(alkyl)_3\overset{+}{N}-CH=CH-\overset{O}{\overset{\|}{C}}-(CH_2)_q-R^3} \quad \underline{A}$$

(which is formed by reacting vinyl halide B

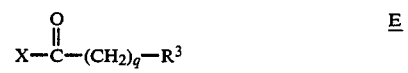  B (wherein X is Cl, Br or I)
with a tertiary amine such as triethylamine, in the presence of ether), employing a molar ratio of VI:A of within the range of from about 1:1 to about 1:1.2, to form the 7-oxabicycloheptane substituted enaminone prostaglandin analog IA' of the invention

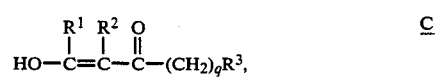  IA'

In practice, amine VI is reacted with the amine salt A without separating A from the reaction mixture originally containing B, tertiary amine and ether solvent.

The starting material B may be prepared by reacting an acyl halide E $$X-\overset{O}{\overset{\|}{C}}-(CH_2)_q-R^3 \quad \underline{E}$$

with acetylene, in a Friedel-Crafts reaction, in the presence of aluminum chloride and an inert organic solvent such as methylene chloride.

As seen from the alternate "A" reaction sequence, compounds of the invention wherein m is 1, p is 1 and $R^1$ and/or $R^2$ are other than hydrogen are prepared by reacting the amine VI with compound C of the structure $$HO-\overset{R^1}{\overset{|}{C}}=\overset{R^2}{\overset{|}{C}}-\overset{O}{\overset{\|}{C}}-(CH_2)_qR^3, \quad \underline{C}$$

which can be expressed as

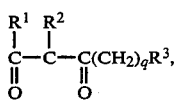

in the presence of an alcohol solvent such as ethanol or methanol, to form IA

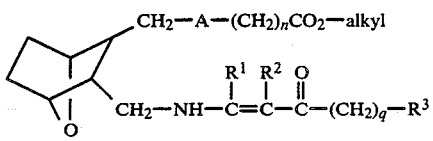

wherein $R^1$ and/or $R^2$ are other than hydrogen.

The starting materials of structure C are known compounds and may be prepared employing the procedure of L. M. Roch, Ann. Chim. 6, 105–161 (1961).

The reaction sequence identified as "B" is employed to prepare comounds of the invention wherein p is 2 to 5, that is,

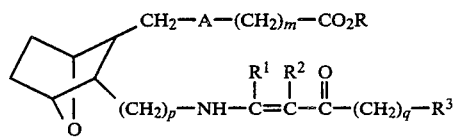

(where p is 2 to 5)

Compound II or IIA is used to form the aldehyde III (where A is —CH=CH—) or IIIA (where A is —(CH$_2$)$_2$). Thus, to form aldehyde III where A is —CH=CH—, comound II is subjected to a Collins oxidation, for example, by reacting II with chromium trioxide in pyridine. To form the aldehyde IIIA (where A is (CH$_2$)$_2$) compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$). The aldehyde III or IIIA is used to prepare a aldehyde IX (where p is 2–5) by carrying out a homologation sequence, such as a Wittig reaction with (C$_6$H$_5$)$_3$P=CHOMe followed by hydrolysis, (p-1) times. The aldehyde IX (where p is 2–5) is then carried on to compounds of this invention where p is 2–5, that is IB, by reducing aldehyde IX by reacting with a reducing agent such as sodium borohydride to form alcohol IXA

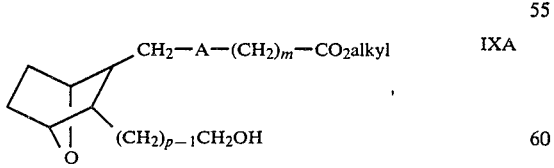

tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

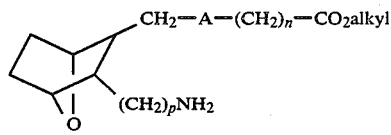

which is then reacted with amine salt A or compound C as described above to form the vinylogous amide compound of the invention IB

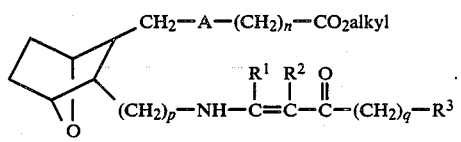

The esters IA, IA' and IB can be converted to the free acid, that is, to

IC (A is —CH=CH—)
ID (A is (CH$_2$)$_2$)

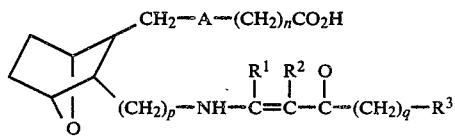

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IC and ID. Each of the formulae set out above which do not include asterisks still represent all of the possible stereosiomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

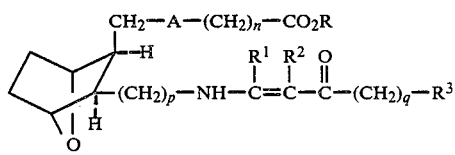

(cis-endo)

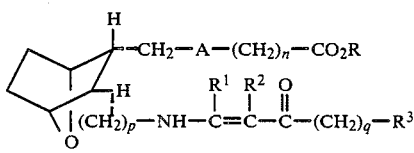

(cis-exo)

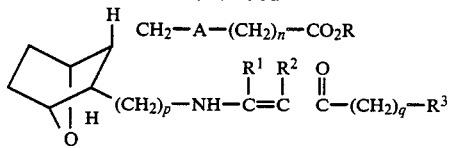

(trans)

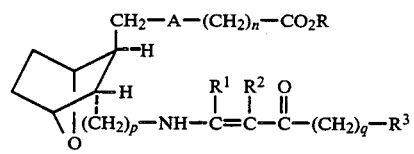

(trans)

The nucleus in each of the compounds of the invention is depicted as

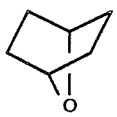

for matter of convenience; it will also be appreciated that the nucleus in the compounds of the invention may be depicted as

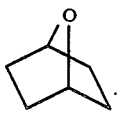

The compounds of this invention are cardiovascular agents useful as platelet aggregation inhibitors (such as in inhibiting arachidonic acid-induced platelet aggregation), e.g., for treatment of thrombolytic disease, such as coronary or cerebral thromboses and in inhibiting bronchoconstriction associated with asthma. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention.

EXAMPLE 1

[1α,2β(Z),3β,4α]-7-[3-[[(3-Oxo-3-phenyl-1-propenyl)amino]methyl]-7-oxabicyclo[2.2.1]hept-2-yl]-5-heptenoic acid, methyl ester

A.

[1α,2β(Z),3β,4α]-7-[3-(Tosyloxymethyl)-7-oxabicyclo[2.2.1]hept-2-yl]-5-heptenoic acid, methyl ester Tosyl chloride (4.256 g, 22.4 mmol) dissolved in $CH_2Cl_2$ (30 ml) was added dropwise to a magnetically stirred solution of [1α,2β(5Z),3β,4α]-7-[3-(hydroxymethyl)-7-oxabicyclo[2.2.1]hept-2-yl]-5-heptenoic acid, methyl ester, prepared as described in U.S. Pat. No. 4,143,054, (3 g, 11.2 mmol) in pyridine (30 ml) at 0° C. After completion of the addition, the reaction was warmed to room temperature and stirred overnight. The reaction was poured into ice/$H_2O$ and stirred for 30 minutes. The products were extracted with EtOAc (80 ml×3). The combined EtOAc layers were washed with 3N-HCl (40 ml×3), saturated $NaHCO_3$, brine and dried over $MgSO_4$. Filtration and evaporation of solvent gave a white solid, which was crystallized from isopropyl ether to give corresponding tosylate in the form of needle crystals (4.23 g, 89%), m.p. 68°–70° C.

B.

[1α,2β(Z),3β,4α]-7-[3-[(Phthalimido)methyl]-7-oxabicyclo[2.2.1]hept-2-yl]-5-heptenoic acid, methyl ester A mixture of title A tosylate (2.86 g, 6.78 mmol) and potassium phthalimide [2.23 g, 12.2 mmol, which had been purified by boiling 5 g with acetone (9 ml) for 15 minutes, filtering hot, washing with 5 ml acetone and drying 6 hours at 100° C. in vacuo] in DMSO (25 ml) was heated at 90°–100° C. for 2 hours. After cooling, water (30 ml) was added. Some material precipitated out. The mixture was filtered through Celite. The filtrate was extracted with ether (3×40 ml). The Celite pad was washed with ether (4×20 ml). The combined ether solutions were washed with water (2×40 ml), dried ($MgSO_4$), filtered and freed of solvent in vacuo leaving 0.87 g of white solid. The Celite filter pad was suspended in ether (40 ml), heated and filtered. This process was repeated. The ether solution was washed with water (2×30 ml), dried and combined with the other material obtained to give 2.66 g of white solid (98.8%). This was recrystallized from ispropyl ether to give title B phthalimide (2.04 g, 75.8%). TLC: silica gel, $Et_2O$-hexane 2:1, UV and vanillin $R_f=0.35$.

C.

[1α,2β(Z),3β,4α]-7-[3-(Aminomethyl)-7-oxabicyclo[2.2.1]hept-2-yl]-5-heptenoic acid, methyl ester Title B phthalimide (2.04 g, 5.14 mmol) was dissolved in distilled $CH_2Cl_2$ (9 ml) and dry distilled EtOH (40 ml) in an argon atmosphere. Anhydrous hydrazine (0.325 ml, 10.3 mmol) was added and the mixture was left stirring overnight at room temperature. The precipitated solid was removed by filtration and washed with more $CH_2Cl_2$. The filtrate was taken to dryness in vacuo leaving a very viscous material (1.97 g). One half of this material was chromatographed on silica gel 60 (50 g), eluting with 4–6% methanol in $CH_2Cl_2$ containing 0.2% $NH_4OH$ to give title amine (256 mg, 37%). TLC: silica gel, 15% MeOH in $CH_2Cl_2+NH_4OH$ (3 drops/10 ml), UV and vanillin $R_f=0.42$.

D. trans-Phenyl 2-chlorovinyl ketone

Benzoyl chloride (15 g, 12.3 ml, 0.107M) was dissolved in $CH_2Cl_2$ (40 ml) and cooled to 0° C. While stirring vigorously with a mechanical stirrer, aluminum chloride (14.25 g, 0.107M) was added portionwise. A brown solution was obtained. The reaction was warmed to room temperature and acetylene gas was bubbled through. While continuing the acetylene flow the temperature was gradually warmed to 40°-50° C. $CH_2Cl_2$ was added several times to replace solvent lost by evaporation. After 6 hours, the reaction mixture was poured into ice (200 ml) and stirred for 15 minutes. The resulting emulsion was filtered through Celite. The pad was washed with more $CH_2Cl_2$ (100 ml). The layers were separated and the aqueous layer was reextracted with $CHCl_3$ (2×100 ml). The combined organic layers were washed with water (2×50 ml), dried ($MgSO_4$) and freed of solvent in vacuo leaving a brown oil. This was distilled to give title chlorovinyl ketone (13 g, 73%), b.p. 96°-100° C./2.3 mm.

E.
[1α,2β(Z),3β,4α]-7-[3-[[(3-Oxo-3-phenyl-1-propenyl)amino]methyl]-7-oxabicyclo[2.2.1]hept-2-yl]-5-heptenoic acid, methyl ester The title D chlorovinyl ketone (332 mg, 2 mmol) was dissolved in distilled ether (7 ml) in an argon atmosphere and cooled in an ice bath. Distilled $Et_3N$ (0.28 ml, 2 mmol) was added. The ice bath was removed and the mixture was stirred at room temperature 2.5 hours. The mixture was cooled in an ice bath and a solution of title C amine (535 mg, 2 mmol) in THF (3 ml) was added. The ice bath was removed. After 4 hours dry $CH_2Cl_2$ (5 ml) was added and the mixture was left stirring overnight at room temperature. More ether was added and the solution was washed with water (3×12 ml), dried ($MgSO_4$) and freed of solvent leaving yellow partially solid material (780 mg). This was chromatographed on silica gel 60 (65 g) eluting with 1% MeOH in $CH_2Cl_2$ to give yellow partially crystalline material (512 mg). This was triturated with ether to give title methyl ester as a white solid (309 mg, 39%). TLC: silica gel, 2% MeOH/$CH_2Cl_2$, UV and vanillin, $R_f$=0.22.

EXAMPLE 2
[1α,2β(Z),3β,4α]-7-[3-[[(3-Oxo-3-phenyl-1-propenyl)amino]methyl]-7-oxabicyclo[2.2.1]hept-2-yl]-5-heptenoic acid The Example 1 methyl ester (296 mg, 0.745 mmol) was dissolved in distilled THF (25 ml) and water (7 ml) in an argon atmosphere. 1N LiOH solution (7.5 ml) was added and the mixture was stirred at room temperature 2.5 hours. 1N HCl solution (7.5 ml) was then added, followed by solid NaCl. The layers were separated. The aqueous layer was extracted with $CHCl_3$ (3×30 ml). The combined organic layers (THF and $CHCl_3$) were washed with saturated NaCl solution (2×30 ml), dried ($MgSO_4$), and freed of solvent in vacuo leaving 323 mg of viscous yellow material. This was chromatographed on silica gel 60 (30 g) eluting with 3% MeOH in $CH_2Cl_2$ to give yellow material (274 mg) which crystallized on addition of ether. This material was crystallized from toluene to give title compound as a pale yellow solid, 199 mg (70%) m.p. 80°-84° (dec.). TLC: silica gel, 5% MeOH in $CH_2Cl_2$, UV and vanillin $R_f$=0.20.

Anal Calcd for $C_{23}H_{29}O_4N.0.2H_2O$: C, 71.36; H, 7.66; N, 3.62 Found: C, 71.45; H, 7.48; N, 3.42

EXAMPLE 3
[1α,2β(Z),3β,4α]-7-[3-[[(1-Methyl-3-oxo-3-phenyl-1-propenyl)amino]methyl]-7-oxabicyclo[2.2.1]hept-2-yl]-5-heptenoic acid, methyl ester The amine prepared in Example 1, part C (401 mg, 1.5 mmol) was dissolved in absolute EtOH (5 ml) in an argon atmosphere. 1-Phenyl-1,3-butanedione (292 mg, 1.8 mmol) (also referred to as 1-phenyl-3-hydroxy-2-buten-1-one) was added and the mixture was left stirring at room temperature for 4 days. The solvent was removed in vacuo and the yellow residue was dissolved in $CH_2Cl_2$. This solution was washed twice with saturated $NaHCl_3$ solution, dried ($MgSO_4$) and freed of solvent in vacuo leaving a yellow oil (680 mg). This was chromatographed on silica gel 60 (40 g), eluting with ether-petroleum ether (1:1) to give title compound as a nearly colorless viscous material (410 mg, 66.4%). TLC: silica gel, $Et_2O$-petroleum ether 2:1, UV and vanillin, $R_f$=0.31.

EXAMPLE 4
[1α,2β(Z),3β,4α]-7-[3-[[(1-Methyl-3-oxo-3-phenyl-1-propenyl)amino]methyl]-7-oxabicyclo[2.2.1]hept-2-yl]-5-heptenoic acid The Example 3 methyl ester (400 mg, 0.97 mmol) was dissolved in distilled THF (35 ml) and water (8 ml) in an argon atmosphere and 1N LiOH solution (9.7 ml) was added. After stirring at room temperature for 3 hours, 1N HCl solution (9.3 ml) was added (pH≈6). Solid NaCl was then added and the layers were separated. The aqueous layer was extracted with $CHCl_3$ (2×70 ml). The combined organic layers (THF and $CHCl_3$) were washed with saturated NaCl solution (2×50 ml), dried ($MgSO_4$), and freed of solvent in vacuo leaving 352 mg of pale yellow oil. This was chromatographed on silica gel 60 (30 g) eluting with 1 and 2% MeOH in $CH_2Cl_2$ to give title compound (283 mg, 73%) as a viscous material which solidified on standing. TLC: silica gel, 5% MeOH in $CH_2Cl_2$, UV and vanillin, $R_f$=0.24.

Anal. Calcd for $C_{24}H_{31}O_4N$: C, 72.52; H, 7.86; N, 3.52 Found: C, 72.13; H, 7.95; N, 3.38

EXAMPLE 5
[1α,2β(Z),3β,4α]-7-[3-[[(2-Methyl-3-oxo-3-phenyl-1-propenyl)amino]methyl]-7-oxabicyclo[2.2.1]hept-2-yl]-5-heptenoic acid, methyl ester

A. 2-Methyl-3-phenyl-3-oxo-propanal

Ref.: L. M. Roch, Ann. Chim. 6, 105-161 (1961).

Sodium (1.25 g, 0.054M) was added portionwise to dry distilled methanol in an argon atmosphere. After cooling the solution in an ice bath, a mixture of distilled propiophenone (6 g, 0.045M) and distilled ethyl formate (3 g, 0.040M) was added dropwise in 10 minutes. The mixture was stirred cold for 30 minutes and then at room temperature. At 2.5 hours an additional 1.0 ml of ethyl formate was added. After 6 hours at room temperature the reaction mixture was kept in the cold room overnight and then stirred an additional 5 hours at room temperature. The solvent was removed in vacuo and the residue was poured into ice water and washed with ether (2×50 ml). The basic aqueous layer was acidified to pH 5 with HOAc. The solid that precipitated was harvested by filtration, washed with more water and dried in vacuo over P$_2$O$_5$ to give title A compound (4.6 g, 63%) as a white crystalline solid (4.6 g, 63%). This was characterized by NMR, IR, and M.S. TLC: silica gel, Et$_2$O-petroleum ether 1:2, UV and I$_2$; R$_f$=0.22.

B.
[1α,2β(Z),3β,4α]-7-[[(2-Methyl-3-oxo-3-phenyl-1-propenyl)amino]methyl]-7-oxabicyclo[2.2.1]hept-2-yl]-5-heptenoic acid, methyl ester The amine prepared in Example 1, Part C, (183 mg, 0.68 mmol) was dissolved in absolute EtOH (2 ml) in an argon atmosphere and title A compound (117 mg, 0.72 mmol) was added. After 4 hours at room temperature, the solvent was removed in vacuo. The yellow residue was dissolved in CH$_2$Cl$_2$, washed twice with saturated NaHCO$_3$ solution, dried (MgSO$_4$) and freed of solvent in vacuo leaving a yellow oil (295 mg). This was chromatographed on silia gel 60 (20 g) eluting with 2% MeOH in CH$_2$Cl$_2$ to give title compound (219 mg, 78%) as a pale yellow oil which was characterized by NMR and M.S. TLC: silica gel, 5% MeOH in CH$_2$Cl$_2$, UV and vanillin; R$_f$=0.54.

EXAMPLE 6

[1α,2β(Z),3β,4α]-7-[[(2-Methyl-3-oxo-3-phenyl-1-propenyl)amino]methyl]-7-oxabicyclo[2.2.1]hept-2-yl]-5-heptenoic acid The Example 5 methyl ester (219 mg, 0.53 mmol) was dissolved in distilled THF (20 ml) and water (5 ml) in an argon atmosphere with a 1N solution of lithium hydroxide (5.3 ml). After stirring at room temperature 2.25 hours the hydrolysis mixture was neutralized by adding 1N HCl solution (5.0 ml, pH 5-6). Solid NaCl was added and the layers were separated. The aqueous layer was extracted with CHCl$_3$ (2×25 ml). The combined organic layers (THF and CHCl$_3$) were washed with saturated NaCl solution (2×25 ml), dried (MgSO$_4$) and freed of solvent in vacuo leaving a yellowish foam (168 mg, 79.7%) which appeared clean on TLC. Silica gel, 10% MeOH in CH$_2$Cl$_2$, UV and vanillin; R$_f$=0.51). This was combined with material from a previous run (using less pure amine) which was contaminated with several minor impurities and chromatographed twice on silica gel 60 (25 g) eluting the first column with 5% MeOH in CH$_2$Cl$_2$ and the second with 2.5% MeOH in CH$_2$Cl$_2$ to give title acid (139 mg) as a light tan solid foam.

Anal. Calcd for C$_{24}$H$_{31}$O$_4$N.0.3H$_2$O: C, 71.54; H, 7.90; N, 3.48 Found: C, 71.32; H, 8.00; N, 3.48
The $^1$H NMR of this material indicates this is a mixture of isomers. (E/Z≃7/3).

EXAMPLE 7

[1α,2β(Z),3β(E),4α]-7-[[(3-Oxo-1-hexenyl)amino]methyl]-7-oxabicyclo[2.2.1]hept-2-yl]-5-heptenoic acid, methyl ester A. trans-Propyl 2-chlorovinyl ketone A solution of distilled butyryl chloride (5 g) in CCl$_4$ (15 ml) was cooled in an ice bath and acetylene was bubbled through the solution. Aluminum chloride (10 g) was added portionwise over a period of two hours. After addition was complete the acetylene stream was continued for 30 minutes while cooling and then 4 hours at room temperature. The dark brown mixture was then poured into ice water (70 ml). More ice and CHCl$_3$ were added. The mixture was filtered through a Celite pad. The pad was washed with more CHCl$_3$. The layers were separated and the organic layer was washed with water (2×50 ml), dried (MgSO$_4$) and freed of solvent in vacuo leaving dark brown material. From this was distilled the desired title chloro compound, 1.73 g (27%), boiling 57°-59° at 10 mm Hg, as a colorless oil which solidified in the freezer.

B.
[1α,2β(Z),3β(E),4α]-7-[3-[[(3-Oxo-1-hexenyl)amino]-methyl]-7-oxabicyclo[2.2.1]hept-2-yl]-5-heptenoic acid, methyl ester The Part A vinyl chloride (273 mg, 2 mmol) was dissolved in 7 ml dry distilled Et$_2$O in an argon atmosphere. After cooling in an ice bath, distilled triethylamine (0.28 ml, 2 mmol) was added. The ice bath was removed and the mixture was stirred at room temperature 2.5 hours. The mixture containing

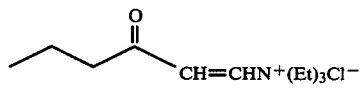

was again cooled in an ice bath and a solution of Example 1, Part A amine (535 mg, 2 mmol) in distilled THF (4 ml) was added. After stirring overnight at room temperature, more ether was added and the solution was washed with water (3×20 ml), dried (MgSO$_4$) and freed of solvent in vacuo leaving a brownish oil (658 mg). This was chromatographed on silica gel (50 g), eluting with ether-petroleum ether (3:1) to give title compound (345 mg, 47%) as an oil which became partially crystalline on standing. TLC, silica gel, 5% MeOH in CH$_2$Cl$_2$, UV and vanillin. R$_f$=0.41 (Streaking).

EXAMPLE 8

[1α,2β(Z),3β,(E),4α]-7-[3-[[(3-Oxo-1-hexenyl)amino]-methyl]-7-oxabicyclo[2.2.1]hept-2-yl]-5-heptenoic acid The Example 7 methyl ester (345 mg, 0.95 mmol) was dissolved in distilled THF (35 ml) and H$_2$O (8 ml) in an argon atmosphere. A solution of 1N LiOH (9.5 ml) was added and the mixture was stirred at room temperature for 3 hours. The reaction was neutralized by adding 1N HCl (9 ml, pH≃6) and solid NaCl was added. The layers were separated and the aqueous layer was extracted with CH$_2$Cl$_2$ (2×60 ml). The combined organic layers (THF and CH$_2$Cl$_2$) were washed with NaCl solution, dried (MgSO$_4$) and freed of solvent in vacuo leaving viscous yellow material (264 mg). This was chromatographed on silica gel (20 g), eluting with 1.5 and 3% MeOH in CH$_2$Cl$_2$ to give title compound (149 mg, 44%) as a yellowish viscous material.

Anal Calcd for C$_{20}$H$_{31}$O$_4$N: C, 68.74, H, 8.94; N, 4.01 Found: C, 68.43; H, 9.02; N, 3.84
TLC: Silica gel, 8% MeOH in CH$_2$Cl$_2$, UV and vanillin, R$_f$=0.48.

EXAMPLE 9

[1β,2α(Z),3β,4β]-7-[3-[[(3-Oxo-3-phenyl-1-propenyl)amino]methyl]-7-oxabicyclo[2.2.1]hept-2-yl]-5-heptenoic acid, methyl ester Following the procedure of Examples 1 and 2, except substituting [1β,2α(Z),3β,4β]-7-[3-(hydroxymethyl)-7-oxabicyclo[2.2.1]hept-2-yl]-5-heptenoic acid, methyl ester prepared as described in U.S. Pat. No. 4,143,054 for [1α,2β(5Z),3β,4α]-7-[3-(hydroxymethyl)-7-oxabicyclo[2.2.1]hept-2-yl]-5-heptenoic acid, methyl ester, the title compound is obtained.

EXAMPLE 10

1β,2α(Z),3β,4β]-7-[3-[[(3-Oxo-3-phenyl-1-propenyl)amino]methyl]-7-oxabicyclo[2.2.1]hept-2-yl]-5-heptenoic acid Following the procedure of Example 2, except substituting the Example 9 methyl ester for the Example 1 methyl ester, the title compound is obtained.

EXAMPLE 11

(1β,2β,3α,4β)-7-[3-[[(3-Oxo-3-phenyl-1-propenyl)amino]methyl]-7-oxabicyclo[2.2.1]hept-2-yl]heptanoic acid

A.

(1β,2β,3β,4β)-7-[3-(Hydroxymethyl)-7-oxabicyclo[2.2.1]hept-2-yl]heptanoic acid

To 800 mg (3.0 mmole) of the [1β,2α(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1β,2β,3α,4β)-7-[3-[[(3-Oxo-3-phenyl-1-propenyl)amino]methyl]-7-oxabicyclo[2.2.1]hept-2-yl]heptanoic acid Following the procedure of Examples 1 and 2 except substituting the Part A alcohol for [1α,2β(5Z),3β,4α]-7-[3-(hydroxymethyl)-7-oxabicyclo[2.2.1]hept-2-yl]-5-heptenoic acid, methyl ester, the title product is obtained.

EXAMPLE 12

[1α,2β(5Z),3β,4α]-7-[3-[[(3-Oxo-3-phenyl-1-propenyl)amino]ethyl]-7-oxabicyclo[2.2.1]hept-2-yl]-5-heptenoic acid

A.

[1α,2β(5Z),3β,4α]-7-[3-(2-Oxo)ethyl]-7-oxabicyclo[2.2.1]hept-2-yl]-5-heptenoic acid, methyl ester Into a dry 1000 ml round bottom 3-necked flask containing a stir bar was added 12.9 g (37.7 mmoles) methoxymethyltriphenylphosphonium chloride ((CH₆H₅)₃P⁺—CH₂OCH₃Cl⁻) and 235 ml distilled toluene (stored over molecular sieves). The resulting suspension was stirred in an ice bath under argon until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1α,2β(5Z),3β,4α]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH₄Cl and extracted with ether (4×200 ml). The combined ether phases were washed with NaCl, saturated solution, and dried (MgSO₄) and concentrated to yield a yellow oil in a white crystalline solid (phosphine oxide). The white solid was triturated with EtOAc and purified by an LP-1 silica column. The fractions obtained were (A) [1α,2β(Z),3β,4α]-7-[3-(2-oxo)ethyl-7-oxabicyclo[2.2.1]hept-2-yl]-5-heptenoic acid, methyl ester, (B) [1α,2β(Z),3β,4α]-7-[3-(2-methoxy)ethenyl-7-oxabicyclo[2.2.1]hept-2-yl]-5-heptenoic acid, methyl ester, and (C) [1α,2β(Z),3β,4α]-7-[3-(2,2-dimethoxy)ethyl-7-oxabicyclo[2.2.1]hept-2-yl]-5-heptenoic acid, methyl ester.

Compounds (B) and (C) were each treated with trifluoroacetic acid to convert each to compound (A).

B.

[1α,2β(Z),3β,4α]-7-[3-(Hydroxyethyl)-7-oxabicyclo[2.2.1]hept-2-yl]-5-heptenoic acid, methyl ester A solution of 266 mg (1 mmol) [1α,2β(5Z),3β,4α]-7-[3-(2-oxo)ethyl-7-oxabicyclo[2.2.1]hept-2-yl]-5-heptenoic acid, methyl ester in 16 ml of methanol is cooled to 0° C. To this stirred solution is added 40 mg of NaBH₄ (1.04 mmol) in one portion. After stirring for 20 minutes, the reaction mixture is poured into 70 ml saturated NH₄Cl solution and is extracted with ethyl acetate (5×40 ml). The combined ethyl acetate extracts are dried over MgSO₄, filtered and concentrated in vacuo to give the title compound.

C.

[1α,2β(Z),3β,4α]-7-[3-[[(3-Oxo-3-phenyl-1-propenyl)amino]ethyl]-7-oxabicyclo[2.2.1]hept-2-yl]-5-heptenoic acid Following the procedure of Examples 1 and 2 except substituting the part B alcohol for [1α,2β(5Z),3β,4α]-7-[3-(hydroxymethyl)-7-oxabicyclo[2.2.1]hept-2-yl]-5-heptenoic acid, methyl ester, the title compound is obtained.

EXAMPLE 13

[1α,2β(Z),3β,4α]-7-[3-[[(3-Oxo-3-phenyl-1-propenyl)amino]butyl]-7-oxabicyclo[2.2.1]hept-2-yl]-5-heptenoic acid

A.

[1α,2β(Z),3β,4α]-7-[3-(3-Oxopropyl)-7-oxabicyclo[2.2.1]hept-2-yl]-5-heptenoic acid, methyl ester

[1α,2β(5Z),3β,4α]-7-[3-(2-Oxoethyl)-7-oxabicyclo[2.2.1]hept-2-yl]-5-heptenoic acid, methyl ester, is treated with methoxymethyltriphenylphosphonium chloride and potassium t-amylate as in Example 12. The product of this reaction is treated with aqueous trifluoroacetic acid to give [1α,2β(5Z),3β,4α]-7-[3-(3-oxopropyl)-7-oxabicyclo[2.2.1]hept-2-yl]-5-heptenoic acid, methyl ester (aldehyde A).

B.

[1α,2β(Z),3β,4α]-7-[3-(4-Oxobutyl)-7-oxabicyclo[2.2.1]hept-2-yl]-5-heptenoic acid, methyl ester Aldehyde A is treated as in part A above to yield the title B aldehyde [1α,2β(Z),3β,4α]-7-[3-(4-oxobutyl)-7-oxabicyclo[2.2.1]hept-2-yl]-5-heptenoic acid, methyl ester.

C.
[1α,2β(Z),3β,4α]-7-[3-(Hydroxybutyl)-7-oxabicyclo[2.2.1]hept-2-yl]-5-heptenoic acid, methyl ester Following the procedure of Example 9 part B except substituting the Example 10 part B aldehyde for the Example 9 part A aldehyde, the title alcohol is obtained.

D.
[1α,2β(5Z),3β,4α]-7-[3-[[(3-Oxo-3-phenyl-1-propenyl)amino]butyl]-7-oxabicyclo[2.2.1]hept-2-yl]-5-heptenoic acid Following the procedure of Examples 1 and 2 except substituting the part C alcohol for [1α,2β(5Z),3β,4α]-7-[3-(hydroxymethyl)-7-oxabicyclo[2.2.1]hept-2-yl]-5-heptenoic acid, methyl ester, the title compound is obtained.

EXAMPLE 14

[1α,2β(Z),3β,4α]-7-[3-[[(3-Benzyl-3-oxo-1-propenyl)amino]methyl]-7-oxabicyclo[2.2.1]hept-2-yl]-5-heptenoic acid Following the procedure of Examples 1 and 2 except substituting phenylacetyl chloride for benzyl chloride, the title compound is obtained.

EXAMPLE 15

[1α,2β(Z),3β,4α]-7-[3-[[(3-Oxo-1-hexenyl)amino]methyl]-7-oxabicyclo[2.2.1]hept-2-yl]-5-heptenoic acid Following the procedure of Examples 1 and 2 except substituting butyryl chloride for benzoyl chloride, the title compound is obtained.

EXAMPLE 16

[1α,2β(Z),3β,4α]-7-[3-[[(3-Cyclohexyl-3-oxo-1propenyl)amino]methyl]-7-oxabicyclo[2.2.1]hept-2-yl]-5-heptenoic acid Following the procedure of Examples 1 and 2 except substituting cyclohexylcarbonyl chloride for benzoyl chloride, the title compound is obtained.

EXAMPLE 17

[1α,2β(Z),3β,4α]-7-[3-[[(3-Benzyl-1-methyl-3-oxo-1-propenyl)amino]methyl]-7-oxabicyclo[2.2.1]hept-2-yl]-5-heptenoic acid Following the procedure of Examples 3 and 4 except substituting 1-phenyl-2,4-pentanedione for 1-phenyl-1,3-butanedione, the title compound is obtained.

EXAMPLE 18

[1α,2β(5Z),3β,4α]-7-[3-[[1-Ethyl-3-oxo-3-pentyl-1-propenyl)amino]methyl]-7-oxabicyclo[2.2.1]hept-2-yl]-5-heptenoic acid Following the procedure of Examples 3 and 4 except substituting 3,5-decadione for 1-phenyl-1,3-butanedione, the title compound is obtained.

EXAMPLE 19

[1α,2β(Z),3β,4α]-7-[3-[[(3-Cyclopentyl-1-methyl-3-oxo-1-propenyl)amino]methyl]-7-oxabicyclo[2.2.1-]hept-2-yl]-5-heptenoic acid Following the procedure of Examples 3 and 4 except substituting 1-cyclopentyl-1,3-butanedione for 1-phenyl-1,3-butanedione, the title compound is obtained.

EXAMPLE 20

[1α,2β(Z),3β,4α]-7-[3-[[(3-Cyclohexyl-2-methyl-3-oxo-1-propenyl)amino]methyl]-7-oxabicyclo[2.2.1]hept-2-yl]-5-heptenoic acid Following the procedure of Examples 5 and 6 except substituting 3-cyclohexyl-2-methyl-3-oxo-propanal for 2-methyl-1-phenyl-1,3-propanedione, the title compound is obtained.

EXAMPLE 21

[1α,2β(Z),3β,4α]-7-[3-[[(3-Benzyl-2-ethyl-3-oxo-1-propenyl)amino]methyl]-7-oxabicyclo[2.2.1]hept-2-yl]-5-heptenoic acid Following the procedure of Examples 5 and 6 except substituting 2-ethyl-3-oxo-4-phenyl-butanal for 2-methyl-1-phenyl-1,3-propanedione, the title compound is obtained.

EXAMPLE 22

[1α,2β(Z),3β,4α]-7-[3-[[(1,2-Dimethyl-3-oxo-3-phenyl-1-propenyl)amino]methyl]-7-oxabicyclo[2.2.1]hept-2-yl]-5-heptenoic acid Following the procedure of Examples 3 and 4 except substituting 1-phenyl-2-methyl-1,3-butanedione for 1-phenyl-1,3-butanedione, the title compound is obtained.

EXAMPLE 23

[1α,2β(Z),3β,4α]-7-[3-[[(3-Cyclohexyl-2-ethyl-1-methyl-3-oxo-1-propenyl)amino]methyl]-7-oxabicyclo[2.2.1-]hept-2-yl]-5-heptenoic acid Following the procedure of Examples 3 and 4 except substituting 1-cyclohexyl-2-ethyl-1,3-butandione for 1-phenyl-1,3-butanedione, the title compound is obtained.

EXAMPLE 24

[1β,2α(Z),3β,4α]-7-[3-[[[(3-Benzyl-1-ethyl-2-methyl-3-oxo-1-propenyl)amino]methyl]-7-oxabicyclo[2.2.1-]hept-2-yl]-5-heptenoic acid Following the procedure of Examples 3 and 4 except substituting 1-phenyl-3-methyl-2,4-hexanedione for 1-phenyl-1,3-butanedione, the title compound is obtained.

EXAMPLE 25

[1β,2α(Z),3β,4β]-7-[3-[[(3-Benzyl-3-oxo-1-propenyl)amino]methyl]-7-oxabicyclo[2.2.1]hept-2-yl]-5-heptenoic acid Following the procedure of Examples 9 and 10 except substituting phenylacetyl chloride for benzoyl chloride, the title compound is obtained.

EXAMPLE 26

[1β,2α(Z),3β,4β]-7-[3-[[(3-Butyl-3-oxo-1-propenyl)amino]methyl]-7-oxabicyclo[2.2.1]hept-2-yl]-5-heptenoic acid Following the procedure of Examples 9 and 10 except substituting valeryl chloride for benzoyl chloride, the title compound is obtained.

EXAMPLE 27

[1β,2α(Z),3β,4β]-7-[3-[[(3-Cyclohexyl-3-oxo-1-propenyl)amino]methyl]-7-oxabicyclo[2.2.1]hept-2-yl]-5-heptenoic acid Following the procedure of Examples 9 and 10 except substituting cyclohexylcarbonyl chloride for benzoyl chloride, title compound is obtained.

EXAMPLE 28

(1β,2β,3α,4β)-7-[3-[[(3-Benzyl-3-oxo-1-propenyl)amino]methyl]-7-oxabicyclo[2.2.1]hept-2-yl]-5-heptanoic acid Following the procedure of Example 11, except substituting phenylacetyl chloride for benzoyl chloride, the title compound is obtained.

EXAMPLE 29

[1α,2β(Z),3β,4α]-7-[3-[[(3-Benzyl-3-oxo-1-propenyl)amino]ethyl]-7-oxabicyclo[2.2.1]hept-2-yl]-5-heptenoic acid Following the procedure of Example 12 except substituting phenylacetyl chloride for benzoyl chloride, the title compound is obtained.

EXAMPLE 30

[1α,2β(Z),3β,4α]-7-[3-[[(1-Methyl-3-oxo-1-propenyl-3-propyl)amino]ethyl]-7-oxabicyclo[2.2.1]hept-2-yl]-5-heptenoic acid Following the procedure of Examples 12, 3 and 4 except substituting 2,3-heptanedione for 1-phenyl-1,3-butanedione, the title compound is obtained.

EXAMPLE 31

[1α,2β(Z),3β,4α]-7-[3-[[(3-Cyclohexyl-1-ethyl-3-oxo-1-propenyl)amino]ethyl]-7-oxabicyclo[2.2.1]hept-2-yl]-5-heptenoic acid Following the procedure of Examples 12, 3 and 4 except substituting 1-cyclohexane-1,3-pentanedione for 1-phenyl-1,3-butanedione, the title compound is obtained.

EXAMPLE 32

[1α,2β(5Z),3β,4α]-7-[3-[[(3-Cyclohexyl-2-methyl-3-oxo-1-propenyl)amino]ethyl]-7-oxabicyclo[2.2.1]hept-2-yl]-5-heptenoic acid Following the procedure of Examples 12, 5 and 6 except substituting 3-cyclohexyl-2-methyl-3-oxo-propanal for 2-methyl-1-phenyl-1,3-propanedione, the title compound is obtained.

EXAMPLE 33

[1α,2β(Z),3β,4α]-7-[3-[[(3-Benzyl-1,2-Dimethyl-3-oxo-1-propenyl)amino]ethyl]-7-oxabicyclo[2.2.1]hept-2-yl]-5-heptenoic acid Following the procedure of Examples 12, 3 and 4 except substituting 3-methyl-5-phenyl-2,4-pentanedione for 1-phenyl-1,3-butanedione, the title compound is obtained.

EXAMPLE 34

[1α,2β(Z),3β,4α]-7-[3-[[(3-Benzyl-3-oxo-1-propenyl)amino]butyl]-7-oxabicyclo[2.2.1]hept-2-yl]-5-heptenoic acid Following the procedure of Example 13 except substituting phenylacetyl chloride for benzoyl chloride, the title compound is obtained.

EXAMPLE 35

[1α,2β(Z),3β,4α]-7-[3-[[(3-Cyclohexyl-3-oxo-1-propenyl)amino]butyl]-7-oxabicyclo[2.2.1]hept-2-yl]-5-heptenoic acid Following the procedure of Example 13 except substituting cyclohexylcarbonyl chloride for benzoyl chloride, the title compound is obtained.

EXAMPLE 36

[1α,2β(Z),3β,4α]-7-[3-[[(3-Benzyl-1-methyl-3-oxo-1-propenyl)amino]butyl]-7-oxabicyclo[2.2.1]hept-2-yl]-5-heptenoic acid Following the procedure of Examples 13, 3 and 4 except substituting 3-methyl-5-phenyl-2,4-pentanedione for 1-phenyl-1,3-butanedione, the title compound is obtained.

EXAMPLE 37

[1α,2β(Z),3β,4α]-7-[3-[[(1-Ethyl-3-oxo-1-propenyl-3-propyl)amino]butyl]-7-oxabicyclo[2.2.1]hept-2-yl]-5-heptenoic acid Following the procedure of Examples 13, 5 and 6 except substituting 3,5-octanedione for 1-phenyl-1,3-butanedione, the title compound is obtained.

EXAMPLE 38

[1α,2β(Z),3β,4α]-7-[3-[[(3-Cyclopropyl-2-methyl-3-oxo-1-propenyl]amino]butyl]-7-oxabicyclo[2.2.1]hept-2-yl]-5-heptenoic acid Following the procedure of Examples 13, 5 and 6 except substituting 3-cyclopropyl-2-methyl-3-oxopropanal propanedione for 2-methyl-1-phenyl-1,3-propanedione, the title compound is obtained.

EXAMPLE 39

[1α,2β(Z),3β,4α]-7-[3-[[(3-Benzyl-1,2-dimethyl-3-oxo-1-propenyl)amino]butyl]-7-oxabicyclo[2.2.1]hept-2-yl]-5-heptenoic acid Following the procedure of Examples 13, 3 and 4 except substituting 3-methyl-1-phenyl-2,4-pentanedione for 1-phenyl-1,3-butanedione, the title compound is obtained.

What is claimed is:

1. A compound having the structural formula

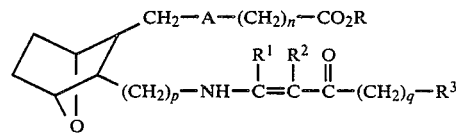

and including all stereoisomers thereof;
wherein A is CH=CH or $(CH_2)_2$;
n is 1 to 8; R is H, lower alkyl or alkali metal; p is 1 to 5; q is 0 to 5; $R^1$ and $R^2$ may be the same or different and are selected from the group consisting of hydrogen, lower alkyl and aralkyl, and $R^3$ is lower alkyl, aryl, aralkyl or cycloalkyl; wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;

the term aryl by itself or as part of another group contains 6 to 10 carbons and is unsubstituted or substituted with lower alkyl, halogen or lower alkoxy;

the term cycloalkyl by itself of as part of another group contains 3 to 12 carbons and is unsubstituted or substituted with 1 or 2 halogens, 1 or 2 lower alkyl groups and/or 1 or 2 lower alkoxy groups; and $(CH_2)_n$, $(CH_2)_p$ and $(CH_2)_q$ may be unsubstituted or include one or more alkyl substituents.

2. The compound as defined in claim 1 having the formula

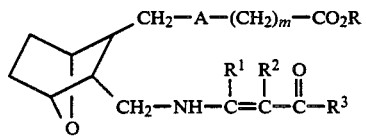

wherein R is hydrogen.

3. The compound as defined in claim 1 wherein m is 1, p is 1, n is 3, A is —CH=CH— and q is 0.

4. The compound as defined in claim 1 wherein A is CH=CH.

5. The compound as defined in claim 1 wherein $R^1$ and $R^2$ are each hydrogen.

6. The compound as defined in claim 1 having the name [1α,2β(5Z),3β,4α]-7-[3-[[(3-oxo-3-phenyl-1-propenyl)amino]methyl-7-oxabicyclo[2.2.1]hept-2-yl]-5-heptenoic acid or the methyl ester thereof, including all stereoisomers thereof.

7. The compound as defined in claim 1 having the name [1α,2β(Z),3β(E),4α]-7-[3-[[(3-oxo-1-hexenyl)amino]methyl]-7-oxabicyclo[2.2.1]hept-2-yl]-5-heptenoic acid or the methyl ester thereof, including all stereoisomers thereof.

8. The compound as defined in claim 1 having the name [1α,2β(Z),3β,4α]-7-[3-[[(2-methyl-3-oxo-3-phenyl-1-propenyl)amino]methyl]-7-oxabicyclo[2.2.1]hept-2-yl]-5-heptenoic acid or the methyl ester thereof, including all stereoisomers thereof.

9. The compound as defined in claim 1 having the name [1α,2β(Z),3β,4α]-7-[3-[[(1-methyl-3-oxo-3-phenyl-1-propenyl)amino]methyl]-7-oxabicyclo[2.2.1]hept-2-yl]-5-heptenoic acid or the methyl ester thereof, including all stereoisomers thereof.

10. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

11. The method as defined in claim 10 wherein said compound is administered in an amount within the range of from about 1 to about 100 mg/kg.

12. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

13. A method of inhibiting platelet aggregation which comprises administering to a mammalian host an effective amount of a compound as defined in claim 1 or a pharmaceutically acceptable salt thereof.

14. A method of inhibiting bronchoconstriction associated with asthma, which comprises administering to a mammalian host an effective amount of a compound as defined in claim 1 or a pharmaceutically acceptable salt thereof.

15. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,533,673
DATED : August 6, 1985
INVENTOR(S) : Masami Nakane

It is certified that error appears in the above—identified patent and that said Letters Patent is hereby corrected as shown below:

Column 4, in reaction scheme B., structure VIII should read

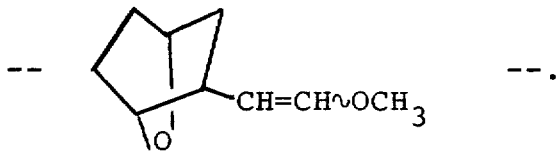

Column 8, the last structure should read

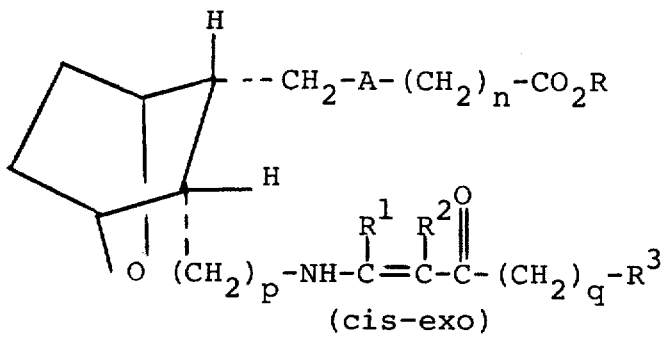

(cis-exo)

Column 18, line 38, "1-cyclohexyl-2-ethyl-1,3-butandione" should read --1-cyclohexyl-2-ethyl-1,3-butanedione--.

Signed and Sealed this

Nineteenth Day of August 1986

[SEAL]

Attest:

DONALD J. QUIGG

Attesting Officer     Commissioner of Patents and Trademarks